United States Patent
Reimer et al.

(10) Patent No.: US 11,284,996 B2
(45) Date of Patent: Mar. 29, 2022

(54) ATTACHMENT OF LEAFLETS TO PROSTHETIC HEART VALVE

(71) Applicant: St. Jude Medical, Cardiology Division, Inc., St. Paul, MN (US)

(72) Inventors: Jay Reimer, Saint Paul, MN (US); Katherine A. Ahmann, Arden Hills, MN (US); Mai Moua, Circle Pines, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 110 days.

(21) Appl. No.: 16/568,345

(22) Filed: Sep. 12, 2019

(65) Prior Publication Data
US 2020/0093590 A1    Mar. 26, 2020

Related U.S. Application Data

(60) Provisional application No. 62/733,902, filed on Sep. 20, 2018.

(51) Int. Cl.
*A61F 2/24* (2006.01)

(52) U.S. Cl.
CPC .......... *A61F 2/2418* (2013.01); *A61F 2/243* (2013.01); *A61F 2220/0075* (2013.01)

(58) Field of Classification Search
CPC ........ A61F 2/2418; A61F 2/2475; A61F 2/07; A61F 2/82; A61F 2/86; A61F 2/90; A61F 2220/0075
See application file for complete search history.

(56) References Cited

U.S. PATENT DOCUMENTS

| | | | |
|---|---|---|---|
| 3,657,744 | A | 4/1972 | Ersek |
| 4,275,469 | A | 6/1981 | Gabbay |

(Continued)

FOREIGN PATENT DOCUMENTS

| | | |
|---|---|---|
| DE | 19857887 A1 | 7/2000 |
| DE | 10121210 B4 | 11/2005 |

(Continued)

OTHER PUBLICATIONS

International Search Report including the Written Opinion from Application No. PCT/US2019/050724 dated Nov. 13, 2019, 11 pages.

(Continued)

*Primary Examiner* — Brian A Dukert
(74) *Attorney, Agent, or Firm* — Lerner, David, Littenberg, Krumholz & Mentlik, LLP

(57) ABSTRACT

A prosthetic mitral valve may include a collapsible stent including a plurality of struts, a plurality of cells arranged in circumferential rows, the circumferential rows including a first row at an outflow end of the stent and a second row at an inflow end of the stent, and a plurality of strut intersections where at least two of the struts connect to one another. A cuff is attached to the stent. A prosthetic valve assembly is adapted to allow blood to flow in only one direction through the valve. The prosthetic valve assembly includes a first prosthetic leaflet having a first end attached directly to a first one of the strut intersections, and a second prosthetic leaflet having a first end attached directly to the first strut intersection. The first strut intersection is partially formed of one of the struts of one of the cells in the first row.

5 Claims, 11 Drawing Sheets

(56) References Cited

U.S. PATENT DOCUMENTS

| | | |
|---|---|---|
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,415,664 A | 5/1995 | Pinchuk |
| 5,480,423 A | 1/1996 | Ravenscroft et al. |
| 5,843,167 A | 12/1998 | Dwyer et al. |
| 5,855,601 A | 1/1999 | Bessler et al. |
| 5,935,163 A | 8/1999 | Gabbay |
| 5,961,549 A | 10/1999 | Nguyen et al. |
| 6,045,576 A | 4/2000 | Starr et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,458,153 B1 | 10/2002 | Bailey et al. |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,652,578 B2 | 11/2003 | Bailey et al. |
| 6,685,625 B2 | 2/2004 | Gabbay |
| 6,716,244 B2 | 4/2004 | Klaco |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 6,951,573 B1 | 10/2005 | Dilling |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,195,641 B2 | 3/2007 | Palmaz et al. |
| 7,247,167 B2 | 7/2007 | Gabbay |
| 7,267,686 B2 | 9/2007 | DiMatteo et al. |
| 7,276,078 B2 | 10/2007 | Spenser et al. |
| 7,311,730 B2 | 12/2007 | Gabbay |
| 7,320,704 B2 | 1/2008 | Lashinski et al. |
| 7,329,278 B2 | 2/2008 | Seguin et al. |
| 7,374,573 B2 | 5/2008 | Gabbay |
| 7,381,218 B2 | 6/2008 | Schreck |
| 7,381,219 B2 | 6/2008 | Salahieh et al. |
| 7,452,371 B2 | 11/2008 | Pavcnik et al. |
| 7,510,572 B2 | 3/2009 | Gabbay |
| 7,510,575 B2 | 3/2009 | Spenser et al. |
| 7,524,331 B2 | 4/2009 | Birdsall |
| 7,534,261 B2 | 5/2009 | Friedman |
| RE40,816 E | 6/2009 | Taylor et al. |
| 7,585,321 B2 | 9/2009 | Cribier |
| 7,628,805 B2 | 12/2009 | Spenser et al. |
| 7,682,390 B2 | 3/2010 | Seguin |
| 7,708,775 B2 | 5/2010 | Rowe et al. |
| 7,731,742 B2 | 6/2010 | Schlick et al. |
| 7,748,389 B2 | 7/2010 | Salahieh et al. |
| 7,780,725 B2 | 8/2010 | Haug et al. |
| 7,799,069 B2 | 9/2010 | Bailey et al. |
| 7,803,185 B2 | 9/2010 | Gabbay |
| 7,824,442 B2 | 11/2010 | Salahieh et al. |
| 7,837,727 B2 | 11/2010 | Goetz et al. |
| 7,846,203 B2 | 12/2010 | Cribier |
| 7,846,204 B2 | 12/2010 | Letac et al. |
| 7,857,845 B2 | 12/2010 | Stacchino et al. |
| 7,892,281 B2 | 2/2011 | Seguin et al. |
| 7,914,569 B2 | 3/2011 | Nguyen et al. |
| 7,959,666 B2 | 6/2011 | Salahieh et al. |
| 7,959,672 B2 | 6/2011 | Salahieh et al. |
| 7,972,378 B2 | 7/2011 | Tabor et al. |
| 7,988,724 B2 | 8/2011 | Salahieh et al. |
| 7,993,394 B2 | 8/2011 | Hariton et al. |
| 8,016,877 B2 | 9/2011 | Seguin et al. |
| D648,854 S | 11/2011 | Braido |
| 8,048,153 B2 | 11/2011 | Salahieh et al. |
| 8,052,741 B2 | 11/2011 | Bruszewski et al. |
| 8,052,749 B2 | 11/2011 | Salahieh et al. |
| 8,052,750 B2 | 11/2011 | Tuval et al. |
| 8,062,355 B2 | 11/2011 | Figulla et al. |
| 8,075,611 B2 | 12/2011 | Millwee et al. |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| 8,137,398 B2 | 3/2012 | Tuval et al. |
| 8,142,497 B2 | 3/2012 | Friedman |
| D660,432 S | 5/2012 | Braido |
| D660,433 S | 5/2012 | Braido et al. |
| D660,967 S | 5/2012 | Braido et al. |
| 8,182,528 B2 | 5/2012 | Salahieh et al. |
| 8,221,493 B2 | 7/2012 | Boyle et al. |
| 8,230,717 B2 | 7/2012 | Matonick |
| 8,231,670 B2 | 7/2012 | Salahieh et al. |
| 8,252,051 B2 | 8/2012 | Chau et al. |
| 8,308,798 B2 | 11/2012 | Pintor et al. |
| 8,313,525 B2 | 11/2012 | Tuval et al. |
| 8,323,335 B2 | 12/2012 | Rowe et al. |
| 8,323,336 B2 | 12/2012 | Hill et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,348,998 B2 | 1/2013 | Pintor et al. |
| 8,366,769 B2 | 2/2013 | Huynh et al. |
| 8,403,983 B2 | 3/2013 | Quadri et al. |
| 8,408,214 B2 | 4/2013 | Spenser |
| 8,414,643 B2 | 4/2013 | Tuval et al. |
| 8,425,593 B2 | 4/2013 | Braido et al. |
| 8,449,599 B2 | 5/2013 | Chau et al. |
| 8,449,604 B2 | 5/2013 | Moaddeb et al. |
| D684,692 S | 6/2013 | Braido |
| 8,454,686 B2 | 6/2013 | Alkhatib |
| 8,500,798 B2 | 8/2013 | Rowe et al. |
| 8,568,474 B2 | 10/2013 | Yeung et al. |
| 8,579,962 B2 | 11/2013 | Salahieh et al. |
| 8,579,966 B2 | 11/2013 | Seguin et al. |
| 8,585,755 B2 | 11/2013 | Chau et al. |
| 8,591,575 B2 | 11/2013 | Cribier |
| 8,597,349 B2 | 12/2013 | Alkhatib |
| 8,603,159 B2 | 12/2013 | Seguin et al. |
| 8,603,160 B2 | 12/2013 | Salahieh et al. |
| 8,613,765 B2 | 12/2013 | Bonhoeffer et al. |
| 8,623,074 B2 | 1/2014 | Ryan |
| 8,652,204 B2 | 2/2014 | Quill et al. |
| 8,663,322 B2 | 3/2014 | Keranen |
| 8,668,733 B2 | 3/2014 | Haug et al. |
| 8,685,080 B2 | 4/2014 | White |
| 8,728,154 B2 | 5/2014 | Alkhatib |
| 8,747,459 B2 | 6/2014 | Nguyen et al. |
| 8,764,820 B2 | 7/2014 | Dehdashtian et al. |
| 8,795,357 B2 | 8/2014 | Yohanan et al. |
| 8,801,776 B2 | 8/2014 | House et al. |
| 8,808,356 B2 | 8/2014 | Braido et al. |
| 8,828,078 B2 | 9/2014 | Salahieh et al. |
| 8,834,563 B2 | 9/2014 | Righini |
| 8,840,661 B2 | 9/2014 | Manasse |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,940,040 B2 | 1/2015 | Shahriari |
| 8,945,209 B2 | 2/2015 | Bonyuet et al. |

(56) References Cited

U.S. PATENT DOCUMENTS

| | | | |
|---|---|---|---|
| 8,961,595 B2 | 2/2015 | Alkhatib | |
| 8,974,523 B2 | 3/2015 | Thill et al. | |
| 8,974,524 B2 | 3/2015 | Yeung et al. | |
| 2002/0036220 A1 | 3/2002 | Gabbay | |
| 2003/0023303 A1 | 1/2003 | Palmaz et al. | |
| 2003/0050694 A1 | 3/2003 | Yang et al. | |
| 2003/0130726 A1 | 7/2003 | Thorpe et al. | |
| 2004/0049262 A1 | 3/2004 | Obermiller et al. | |
| 2004/0093075 A1 | 5/2004 | Kuehne | |
| 2004/0111111 A1 | 6/2004 | Lin | |
| 2004/0210304 A1 | 10/2004 | Seguin et al. | |
| 2004/0260389 A1 | 12/2004 | Case et al. | |
| 2005/0096726 A1 | 5/2005 | Sequin et al. | |
| 2005/0137682 A1 | 6/2005 | Justino | |
| 2005/0137695 A1 | 6/2005 | Salahieh et al. | |
| 2005/0137697 A1 | 6/2005 | Salahieh et al. | |
| 2005/0203605 A1 | 9/2005 | Dolan | |
| 2005/0240200 A1 | 10/2005 | Bergheim | |
| 2005/0256566 A1 | 11/2005 | Gabbay | |
| 2006/0008497 A1 | 1/2006 | Gabbay | |
| 2006/0074484 A1 | 4/2006 | Huber | |
| 2006/0122692 A1 | 6/2006 | Gilad et al. | |
| 2006/0149360 A1 | 7/2006 | Schwammenthal et al. | |
| 2006/0161249 A1 | 7/2006 | Realyvasquez et al. | |
| 2006/0173532 A1 | 8/2006 | Flagle et al. | |
| 2006/0178740 A1 | 8/2006 | Stacchino et al. | |
| 2006/0195180 A1 | 8/2006 | Kheradvar et al. | |
| 2006/0206202 A1 | 9/2006 | Bonhoeffer et al. | |
| 2006/0241744 A1 | 10/2006 | Beith | |
| 2006/0259120 A1 | 11/2006 | Vongphakdy et al. | |
| 2006/0259137 A1 | 11/2006 | Artof et al. | |
| 2006/0265056 A1 | 11/2006 | Nguyen et al. | |
| 2006/0276813 A1 | 12/2006 | Greenberg | |
| 2006/0276874 A1 | 12/2006 | Wilson et al. | |
| 2007/0010876 A1 | 1/2007 | Salahieh et al. | |
| 2007/0027534 A1 | 2/2007 | Bergheim et al. | |
| 2007/0043435 A1 | 2/2007 | Seguin et al. | |
| 2007/0055358 A1 | 3/2007 | Krolik et al. | |
| 2007/0067029 A1 | 3/2007 | Gabbay | |
| 2007/0093890 A1 | 4/2007 | Eliasen et al. | |
| 2007/0100435 A1 | 5/2007 | Case et al. | |
| 2007/0118210 A1 | 5/2007 | Pinchuk | |
| 2007/0213813 A1 | 9/2007 | Von Segesser et al. | |
| 2007/0233228 A1 | 10/2007 | Eberhardt et al. | |
| 2007/0244545 A1 | 10/2007 | Birdsall et al. | |
| 2007/0244552 A1 | 10/2007 | Salahieh et al. | |
| 2007/0288087 A1 | 12/2007 | Fearnot et al. | |
| 2008/0021552 A1 | 1/2008 | Gabbay | |
| 2008/0039934 A1 | 2/2008 | Styrc | |
| 2008/0071369 A1 | 3/2008 | Tuval et al. | |
| 2008/0082164 A1 | 4/2008 | Friedman | |
| 2008/0097595 A1 | 4/2008 | Gabbay | |
| 2008/0114452 A1 | 5/2008 | Gabbay | |
| 2008/0125853 A1 | 5/2008 | Bailey et al. | |
| 2008/0140189 A1 | 6/2008 | Nguyen et al. | |
| 2008/0147183 A1 | 6/2008 | Styrc | |
| 2008/0154355 A1 | 6/2008 | Benichou et al. | |
| 2008/0154356 A1 | 6/2008 | Obermiller et al. | |
| 2008/0243245 A1 | 10/2008 | Thambar et al. | |
| 2008/0255662 A1 | 10/2008 | Stacchino et al. | |
| 2008/0262602 A1 | 10/2008 | Wilk et al. | |
| 2008/0269879 A1 | 10/2008 | Sathe et al. | |
| 2009/0099653 A1 | 4/2009 | Suri et al. | |
| 2009/0112309 A1 | 4/2009 | Jaramillo et al. | |
| 2009/0138079 A1 | 5/2009 | Tuval et al. | |
| 2009/0254175 A1 | 10/2009 | Quijano et al. | |
| 2009/0276027 A1 | 11/2009 | Glynn | |
| 2010/0004740 A1 | 1/2010 | Seguin et al. | |
| 2010/0036484 A1 | 2/2010 | Hariton et al. | |
| 2010/0049306 A1 | 2/2010 | House et al. | |
| 2010/0087907 A1 | 4/2010 | Lattouf | |
| 2010/0131055 A1 | 5/2010 | Case et al. | |
| 2010/0168778 A1 | 7/2010 | Braido | |
| 2010/0168839 A1 | 7/2010 | Braido et al. | |
| 2010/0168844 A1 | 7/2010 | Toomes et al. | |
| 2010/0185277 A1 | 7/2010 | Braido et al. | |
| 2010/0191326 A1 | 7/2010 | Alkhatib | |
| 2010/0204781 A1 | 8/2010 | Alkhatib | |
| 2010/0204785 A1 | 8/2010 | Alkhatib | |
| 2010/0217382 A1 | 8/2010 | Chau et al. | |
| 2010/0234940 A1 | 9/2010 | Dolan | |
| 2010/0249911 A1 | 9/2010 | Alkhatib | |
| 2010/0249923 A1 | 9/2010 | Alkhatib et al. | |
| 2010/0286768 A1 | 11/2010 | Alkhatib | |
| 2010/0298931 A1 | 11/2010 | Quadri et al. | |
| 2011/0029072 A1 | 2/2011 | Gabbay | |
| 2011/0054466 A1 | 3/2011 | Rothstein et al. | |
| 2011/0098800 A1 | 4/2011 | Braido et al. | |
| 2011/0098802 A1 | 4/2011 | Braido et al. | |
| 2011/0137397 A1 | 6/2011 | Chau et al. | |
| 2011/0172765 A1 | 7/2011 | Nguyen et al. | |
| 2011/0208283 A1 | 8/2011 | Rust | |
| 2011/0264206 A1 | 10/2011 | Tabor | |
| 2012/0035722 A1 | 2/2012 | Tuval | |
| 2012/0078347 A1 | 3/2012 | Braido et al. | |
| 2012/0101572 A1 | 4/2012 | Kovalsky et al. | |
| 2012/0123529 A1 | 5/2012 | Levi et al. | |
| 2012/0303116 A1 | 11/2012 | Gorman, III et al. | |
| 2013/0261740 A1 | 10/2013 | Eberhardt et al. | |
| 2013/0274873 A1 | 10/2013 | Delaloye et al. | |
| 2014/0121763 A1 | 5/2014 | Duffy et al. | |
| 2014/0155997 A1 | 6/2014 | Braido | |
| 2014/0214159 A1 | 7/2014 | Vidlund et al. | |
| 2014/0228946 A1 | 8/2014 | Chau et al. | |
| 2014/0303719 A1 | 10/2014 | Cox et al. | |
| 2014/0324164 A1 | 10/2014 | Gross et al. | |
| 2014/0343671 A1 | 11/2014 | Yohanan et al. | |
| 2014/0350668 A1 | 11/2014 | Delaloye et al. | |
| 2014/0350669 A1 | 11/2014 | Gillespie et al. | |
| 2015/0073545 A1* | 3/2015 | Braido | A61F 2/2412 623/2.18 |
| 2015/0127100 A1* | 5/2015 | Braido | A61F 2/2418 623/2.38 |

FOREIGN PATENT DOCUMENTS

| | | |
|---|---|---|
| DE | 102005003632 A1 | 8/2006 |
| DE | 202008009610 U1 | 12/2008 |
| EP | 0850607 A1 | 7/1998 |
| EP | 1000590 A1 | 5/2000 |
| EP | 1584306 A1 | 10/2005 |
| EP | 1598031 A2 | 11/2005 |
| EP | 1360942 B1 | 12/2005 |
| EP | 1926455 A2 | 6/2008 |
| EP | 2537487 A1 | 12/2012 |
| FR | 2850008 A1 | 7/2004 |
| FR | 2847800 B1 | 10/2005 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 01028459 A1 | 4/2001 |
| WO | 2001049213 A2 | 7/2001 |
| WO | 0154625 A1 | 8/2001 |
| WO | 01056500 A2 | 8/2001 |
| WO | 0176510 A2 | 10/2001 |
| WO | 2002036048 A1 | 5/2002 |
| WO | 0247575 A2 | 6/2002 |
| WO | 02067782 A2 | 9/2002 |
| WO | 03047468 A1 | 6/2003 |
| WO | 2005070343 A1 | 8/2005 |
| WO | 06073626 A2 | 7/2006 |
| WO | 07071436 A2 | 6/2007 |
| WO | 08070797 A2 | 6/2008 |
| WO | 10008548 A2 | 1/2010 |
| WO | 2010008549 A1 | 1/2010 |
| WO | 2010096176 A1 | 8/2010 |
| WO | 2010098857 A1 | 9/2010 |

OTHER PUBLICATIONS

"Catheter-Implanted Prosthetic Heart Valves: Transluminal Catheter Implantation of a New Expandable Artificial Heart Valve in the

(56) References Cited

OTHER PUBLICATIONS

Descending Thoracic Aorta In Isolated Vessels and Closed Chest Pigs", Knudsen et al., The International Journal of Artificial Organs, vol. 16, No. 5, May 1993, pp. 253-262 (profiled at 1,798,509).

"Closed Heart Surgery: Back to the Future", Samuel V. Lichtenstein, The Journal of Thoracic and Cardiovascular Surgery, vol. 131, No. 5, May 2006, pp. 941-943. (profiled at 5635963).

"Direct-Access Valve Replacement", Christoph H. Huber, et al., Journal of the American College of Cardiology, vol. 46, No. 2, (Jul. 19, 2005). (profiled at 3,729,371).

"Minimally invasive cardiac surgery", M. J. Mack, Surgical Endoscopy, 2006, 20:S488-S492, DOI: 10.1007/s00464-006-0110-8 (presented Mar. 23, 2006) (profiled at 3,717,330).

"Percutaneous Aortic Valve Implantation Retrograde From the Femoral Artery", John G. Webb et al., Circulation, 2006; 113:842-850 (Feb. 6, 2006). (profiled at 3,827,967).

"Percutaneous Aortic Valve Replacement: Resection Before Implantation", Quaden, Rene et al., European J. of Cardio-Thoracic Surgery, vol. 27, No. 5, May 2005, pp. 836-840 (profiled at 1,039,678).

"Transapical aortic valve implantation: an animal feasibility study"; Todd M. Dewey et al., The annals of thoracic surgery 2006; 82: 110-6 (Feb. 13, 2006). (profiled at 3,717,325).

"Transapical Approach for Sutureless Stent-Fixed Aortic Valve Implantation: Experimental Results", Th. Walther et al., European Journal of Cardio-Thoracic Surgery, vol. 29, No. 5, May 2006, pp. 703-708. (profiled at 3,717,332).

"Transapical Transcatheter Aortic Valve Implantation in Humans", Samuel V. Lichtenstein et al., Circulation. 2006; 114: 591-596 (Jul. 31, 2006) (profiled at 3,831,615).

"Transcatheter Umbrella Closure of Valvular and Paravalvular Leaks", Hourihan et al., Journal of the American College of Cardiology, vol. 20, No. 6, Nov. 1992, pp. 1371-1377.

"Transluminal Aortic Valve Placement. A Feasability Study with a Newly Designed Collapsible Aortic Valve", Moazami et al., ASAIO Journal, vol. 42, No. 5, 1996, pp. M381-M385 (profiled at 1,798,531).

"Transluminal Catheter Implanted Prosthetic Heart Valves", Andersen, H. R., International Journal of Angiology, vol. 7, No. 2, Mar. 1998, pp. 102-106 (profiled at 1,798,541).

"Transluminal Implantation of Artificial Heart Valves", Andersen, H. R., et al., European Heart Journal, vol. 13, No. 5, May 1992, pp. 704-708 (profiled at 1,805,328).

Buellesfeld et al., "Treatment of Paravalvular Leaks Through Inverventional Techniques", Multimedia Manual of Cardithoracic Surgery, Department of Cardiology, Ben University Hospital, Jan. 2011.

De Cicco, et al., "Aortic Valve Periprosthetic Leakage: Anatomic Observations and Surgical Results", The Annals of Thoracic Surgery, vol. 79, No. 5, May 2005, pp. 1480-1485.

Gössl and Rihal, "Percutaneous Treatment of Aortic and Mitral Valve Paravalvular Regurgitation", Current Cardiology Reports, vol. 15, No. 8, Aug. 2013, pp. 1-8.

Heat Advisor, "Heart repairs without surgery. Minimally invasive procedures aim to correct valve leakage", Sep. 2004, PubMed ID 15586429.

Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008 (profiled at 1,039,679).

Muñoz, Daniel Rodríguez, Carla Lázaro Rivera, and José Luis Zamorano Gómez, "Guidance of Treatment of Perivalvular Prosthetic Leaks", Current Cardiology Reports, vol. 16, No. 1, Nov. 2013, pp. 1-6.

Rohde, I., Masch, J.-M., Theisen-Kunde, D., Marczynski-Bühlow, M., Bombien Quaden, R., Lutter, G. and Brinkmann, R., "Resection of Calcified Aortic Heart Leaflets In Vitro by Q-Switched 2?μm Microsecond Laser Radiation", Journal of Cardiac Surgery, vol. 30, No. 2, Feb. 2015, pp. 157-162. doi: 10.1111/jocs.12481.

Ruiz, Carlos, Overview of PRE-CE Mark Transcatheter Aortic Valve Technologies, Euro PCR (powerpoint profiled at 1,389,233)—dated May 25, 2010?

Swiatkiewicz et al., "Percutaneous Closure of Mitral Perivalvular Leak", Kardiologia Polska, vol. 67, No. 7, 2009, pp. 762-764.

Transcatheter Valve Repair, Hijazi et al., CRC Press, Jan. 2006, pp. 165-186. (profiled at 4,174,242).

U.S. Appl. No. 29/375,243—Braido, et al., U.S. Appl. No. 29/375,243, filed Sep. 20, 2010, titled "Surgical Stent Assembly".

\* cited by examiner

ATTACHMENT OF LEAFLETS TO PROSTHETIC HEART VALVE

CROSS-REFERENCE TO RELATED APPLICATIONS

This application claims the benefit of the filing date of U.S. Provisional Patent Application No. 62/733,902 filed Sep. 20, 2018, the disclosure of which is hereby incorporated by reference herein.

BACKGROUND

The present disclosure relates to heart valve replacement and, in particular, to collapsible prosthetic heart valves. More particularly, the present disclosure relates to collapsible prosthetic heart valves having designs that facilitate attachment of a valve assembly to a stent.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the valve, assuring its proper location, and then expanding a balloon positioned within the valve stent. For self-expanding valves, on the other hand, the stent automatically expands as the sheath covering the valve is withdrawn.

Typically, two adjacent leaflets of a prosthetic valve assembly form a commissure which is attached, for example by sutures, to a corresponding commissure attachment feature ("CAF") of the stent of the prosthetic heart valve. CAFs are often larger or bulkier than other portions of the stent. It is typically desirable for the prosthetic heart valve to be collapsible to a small profile for transcatheter delivery, and a bulky CAF may result in a larger collapsed profile of the prosthetic heart valve compared to a less bulky CAF. Also, the position of the CAF within the prosthetic heart valve may result in undesirable interference between the CAF and the native anatomy upon implantation of the prosthetic heart valve. Thus, it may be desirable to provide a prosthetic heart valve that allows for secure attachment of leaflet commissures to the stent while minimizing the profile of the stent and reducing or eliminating the likelihood of interference between the CAFs and the native anatomy.

BRIEF SUMMARY

According to an aspect of the disclosure, a prosthetic mitral valve includes a collapsible stent, a cuff, and a prosthetic valve assembly. The stent includes a plurality of struts, a plurality of cells arranged in circumferential rows, the circumferential rows including a first row at an outflow end of the stent and a second row at an inflow end of the stent, and a plurality of strut intersections where at least two of the struts connect to one another. The cuff is attached to the stent. The prosthetic valve assembly is adapted to allow blood to flow from the inflow end of the stent toward the outflow end of the stent and to restrict blood from flowing from the outflow end of the stent toward the inflow of the stent. The prosthetic valve assembly includes a first prosthetic leaflet having a first end attached directly to a first one of the strut intersections, and a second prosthetic leaflet having a first end attached directly to the first strut intersection. The first strut intersection is partially formed of one of the struts of one of the cells in the first row.

DETAILED DESCRIPTION

As used herein, the term "inflow end," when used in connection with a prosthetic heart valve, refers to the end of the heart valve through which blood first passes during antegrade blood flow, whereas the term "outflow end," when used in connection with a prosthetic heart valve, refers to the end of the heart valve through which blood last passes during antegrade blood flow. The term "circumferential," when used in connection with a prosthetic heart valve, refers to the direction around the perimeter of the valve. The term "leading end," when used in connection with a suture, refers to the end initially advanced through a material, while the term "trailing end" refers to the opposite end.

Figure 1A:
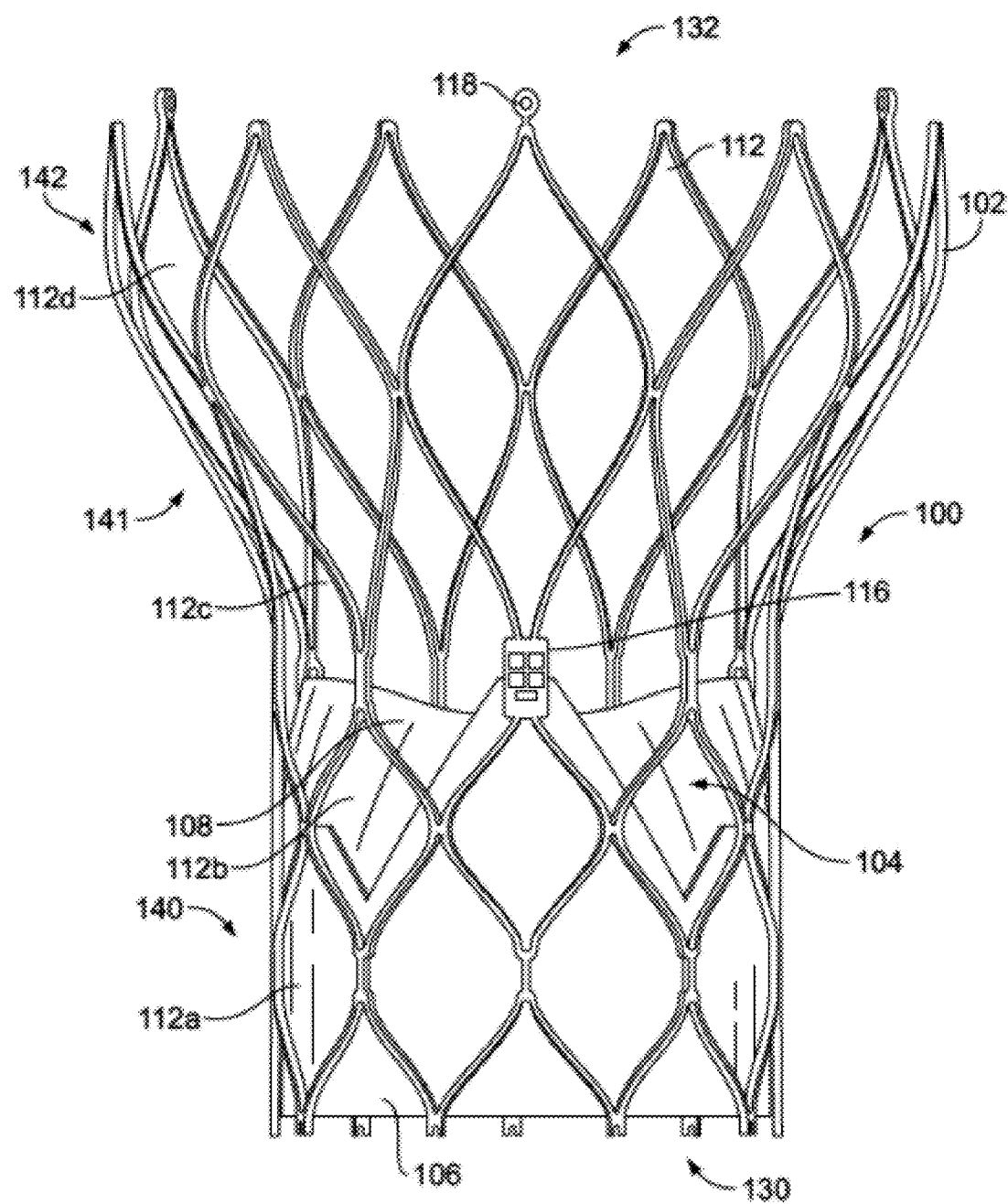
FIG. 1A is a side elevational view of a conventional prosthetic heart valve.

FIG. 1A shows a collapsible stent-supported prosthetic heart valve 100 known in the art. Prosthetic heart valve 100 is designed to replace the function of a native tricuspid, bicuspid or unicuspid valve of a patient, such as a native aortic valve. Prosthetic heart valve 100 includes expandable stent 102, which may be formed from biocompatible materials that are capable of self-expansion, such as, for example, shape memory alloys such as nitinol. Stent 102 extends from a proximal or annulus end 130 to a distal or aortic end 132, and includes tubular annulus section 140 adjacent the proximal end and aortic section 142 adjacent the distal end. Annulus section 140 has a relatively small cross-section in the expanded condition, while aortic section 142 has a relatively large cross-section in the expanded condition. Preferably, annulus section 140 is in the form of a cylinder having a substantially constant diameter along its length. Transition section 141 may taper outwardly from annulus section 140 to aortic section 142. Each of the sections of stent 102 includes a plurality of cells 112 connected to one another in one or more annular rows around the stent. For example, as shown in FIG. 1A, annulus section 140 may include a first proximalmost circumferential row of cells 112a and a second circumferential row of cells 112b positioned distal to the first row of cells. Aortic section 142 may include a circumferential row of cells 112d, which may be the distalmost row of cells. An intermediate circumferential row of cells 112c may be positioned between the proximalmost row of cells 112a and the distalmost row of cells 112d. Cells 112d in aortic section 142 may be larger than cells 112a, 112b in annulus section 140. The larger cells in aortic section 142 better enable prosthetic valve 100 to be positioned in the native valve annulus without the stent structure interfering with blood flow to the coronary arteries.

Stent 102 may include one or more retaining elements 118 at distal end 132 thereof, the retaining elements being sized and shaped to cooperate with retaining structures provided on the deployment device (not shown). The engagement of retaining elements 118 with retaining structures on the deployment device helps maintain prosthetic heart valve 100 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and the heart valve is deployed. In some variations, retaining elements 118 may be disposed near proximal end 130 of heart valve 100.

Prosthetic heart valve 100 includes a valve assembly 104, preferably positioned in the annulus section 140 of stent 102 and secured to the stent. Valve assembly 104 may include a cuff 106 and a plurality of prosthetic valve elements, such as leaflets 108, which collectively function as a one-way valve by coapting with one another, generally allowing blood to flow in an antegrade direction from proximal end 130 to distal end 132, while substantially blocking blood from flowing in a retrograde direction from the distal end to the proximal end. As a prosthetic aortic valve, valve 100 has three leaflets 108. However, it will be appreciated that other prosthetic heart valves with which the present disclosure may be used may have more or fewer leaflets.

Although cuff 106 is shown in FIG. 1A as being disposed on the luminal or inner surface of annulus section 140, it is contemplated that the cuff may be disposed on the abluminal or outer surface of the annulus section or may cover all or part of either or both of the luminal and abluminal surfaces. Both cuff 106 and leaflets 108 may be wholly or partly formed of any suitable biological material or polymer such as, for example, bovine or porcine pericardial tissue or polytetrafluoroethylene (PTFE).

Figure 1B:
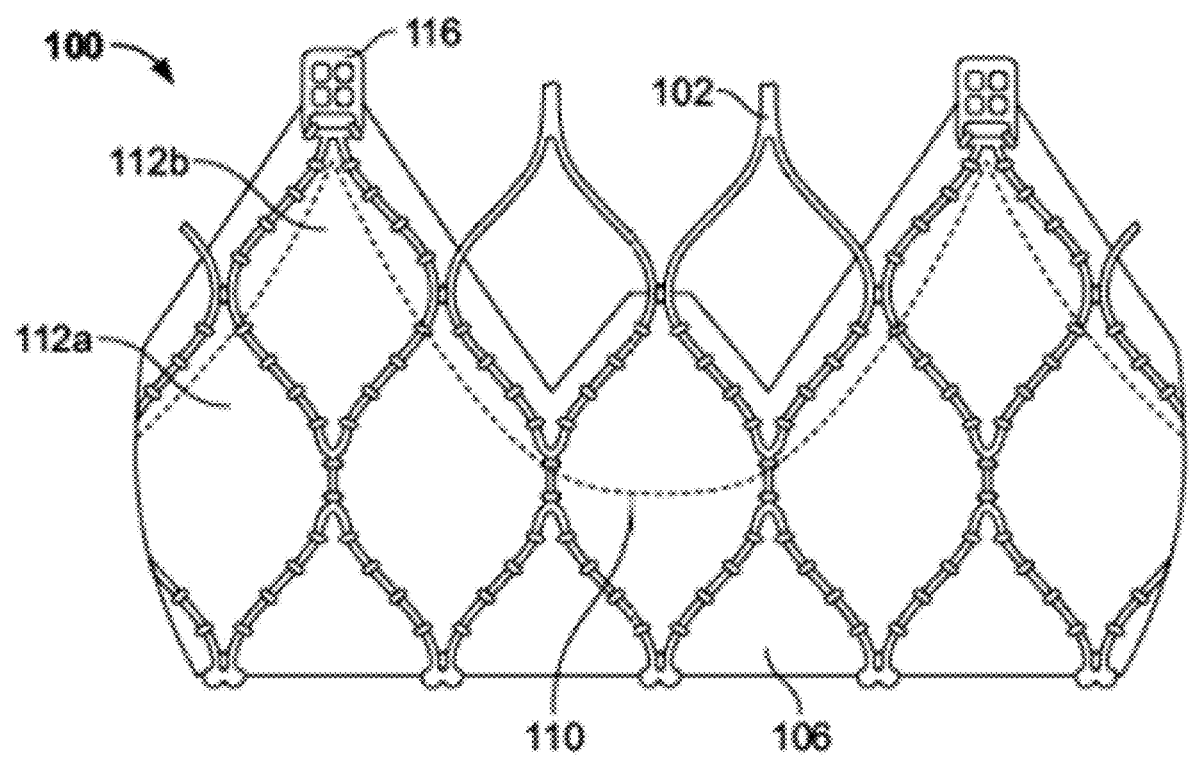
FIG. 1B is a schematic developed view of a portion of the prosthetic heart valve of FIG. 1A.

Leaflets 108 may be attached along their belly portions 110 to cells 112 of stent 102, with the commissure between adjacent leaflets attached to CAFs 116. This is shown in FIG. 1B. As can be seen in FIG. 1A, each CAF 116 may lie at the intersection of four cells 112 of stent 102, two of the cells being adjacent one another in the same annular row, and the other two cells being in different annular rows and lying in an end-to-end relationship. Preferably, CAFs 116 are positioned entirely within the annulus section 140 of stent 102 or at the juncture of annulus section 140 and transition section 141, although they may be positioned above the annulus section. CAFs 116 may include one or more eyelets which facilitate the suturing of the leaflet commissure to the stent.

In the illustrated embodiment, CAFs 116 are formed by stent 102, or, in other words, are unitary or integral with the body of the stent. This may be achieved by, for example, laser cutting stent 102, including CAFs 116, from a single piece of material. CAFs 116 may add to the profile of valve 100 compared to an identical valve without the CAFs. CAFs 116 may also reduce the ability of stent body 102 to bend to match the anatomy during delivery, such as when the valve 100 is delivered through the aortic arch. This ability to bend or otherwise conform to the anatomy may be referred to as tracking ability. Because of their relative stiffness compared to the remainder of stent 102, CAFs 116 may also raise the likelihood of vessel trauma or particulate dislodgement, which may result in problems such as stroke. However, if CAFs 116 are not included in stent body 102, another method of attaching leaflets 108 to the stent may be required.

Prosthetic heart valve 100 may be used to replace, for example, a native aortic valve, a surgical heart valve, or a heart valve that has undergone a surgical procedure. The prosthetic heart valve may be delivered to the desired site (e.g., near the native aortic annulus) using any suitable delivery device. During delivery, the prosthetic heart valve is disposed inside the delivery device in the collapsed condition. The delivery device may be introduced into a patient using a transfemoral, transapical, transseptal, transaortic, subclavian, or any other percutaneous approach. Once the delivery device has reached the target site, the user may deploy prosthetic heart valve 100. Upon deployment, prosthetic heart valve 100 expands so that annulus section 140 is in secure engagement within the native aortic annulus. When the prosthetic heart valve is properly positioned inside the heart, it works as a one-way valve, allowing blood to flow from the left ventricle of the heart to the aorta, and preventing blood from flowing in the opposite direction.

Figure 1C:
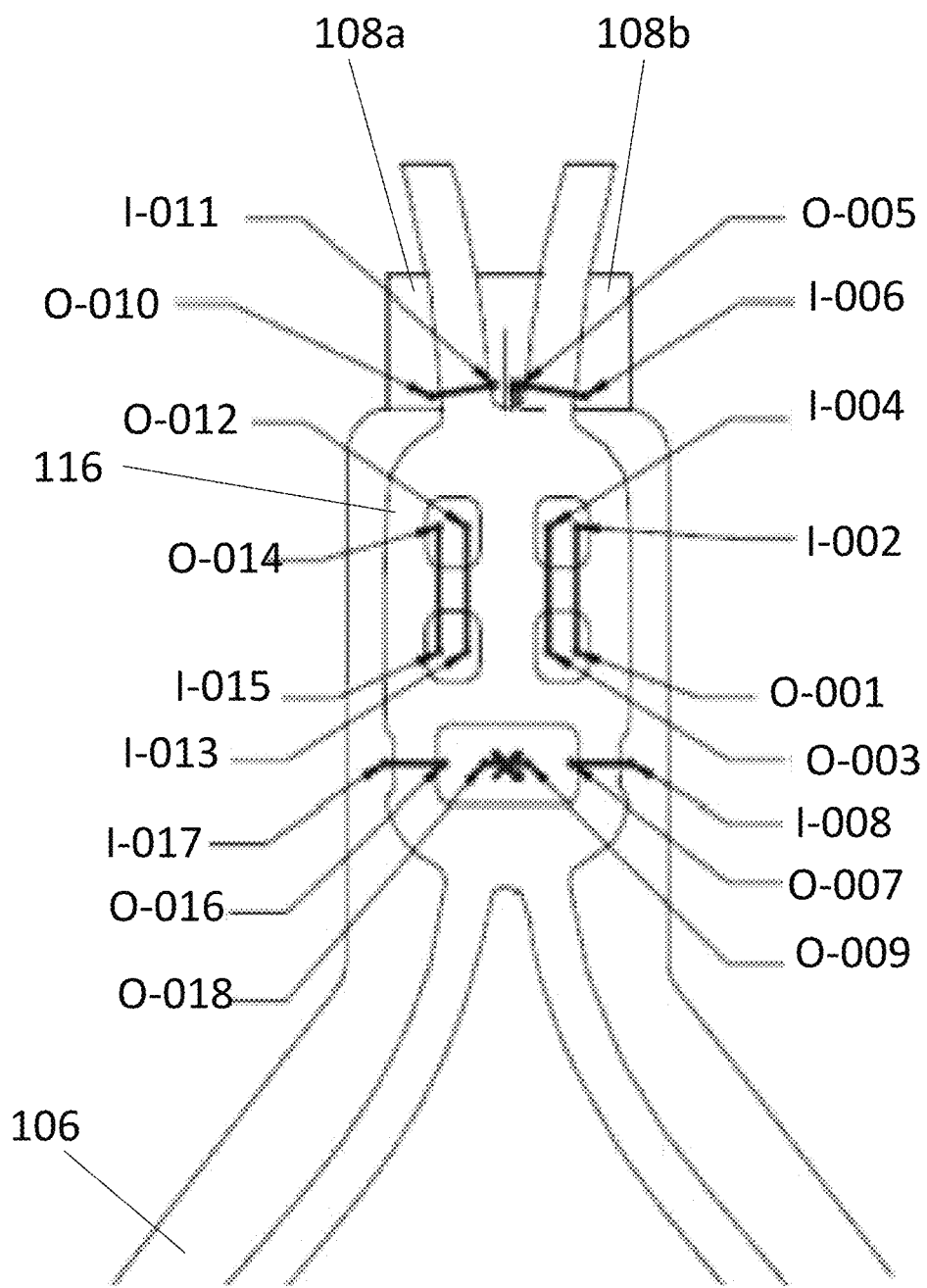
FIG. 1C is a schematic view of a suture pattern attaching two leaflets to a CAF in the prosthetic heart valve of FIG. 1A, shown from the exterior of the prosthetic heart valve.
Figure 1D:
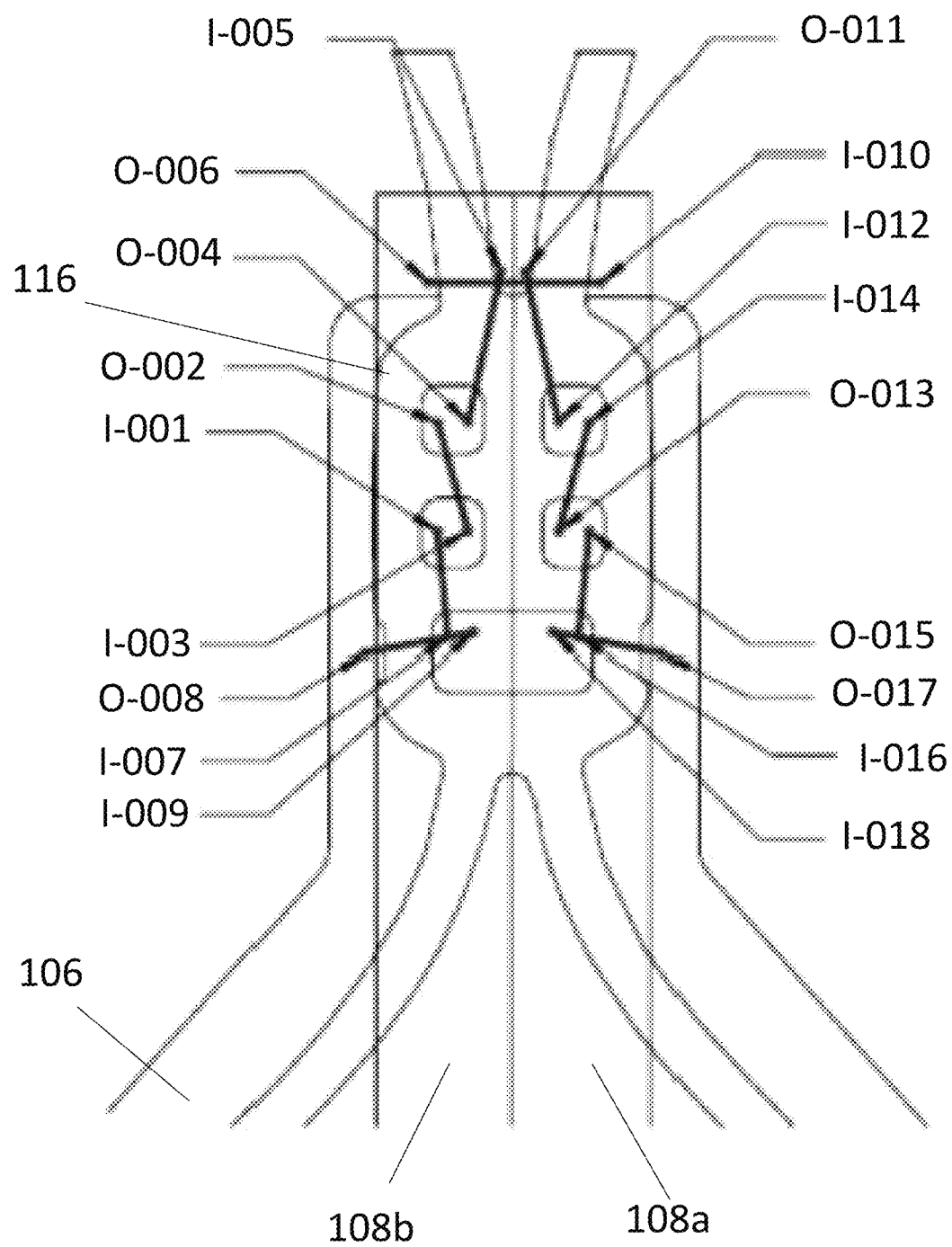
FIG. 1D is a schematic view of the suture pattern of FIG. 1C, shown from the interior of the prosthetic heart valve.

FIGS. 1C-D illustrate an example of a suture pattern for attaching two adjacent leaflets 108 of valve assembly 104 to one of CAFs 116. As illustrated, CAF 116 includes four relatively small eyelets positioned in a two-by-two grid (i.e., two rows and two columns), with an elongated eyelet positioned below the four smaller eyelets. It is preferred that a single suture be used to couple first leaflet 108a and second leaflet 108b to cuff 106 and CAF 116, but it should be understood that multiple sutures may also be suitable. FIG. 1C illustrates CAF 116 as viewed from the exterior of prosthetic heart valve 100, whereas FIG. 1D illustrates the CAF as viewed from the interior of the prosthetic heart valve. As should be understood from the figures, an extension of cuff 106 is positioned between CAF 116 and leaflets 108a, 108b.

The suture pattern of FIGS. 1C-D is described and illustrated with reference to part numbers having the format of I-001 or O-001. The "I" refers to an end of a suture being passed inwardly through cuff 106 and/or leaflets 108a, 108b in the particular view being shown, the "O" refers to an end of the suture being passed outwardly through the cuff and/or leaflets in the particular view being shown, and the number (e.g., 001) refers to the sequence of the particular stitch being described starting with "001." Referring to FIGS. 1C-D, the suture pattern may begin by passing the suture through leaflet 108b and cuff 106 at point I-001 (FIG. 1D), with the leading end of the suture exiting at point O-001 (FIG. 1C). The suture may be inserted at point I-002 (FIG. 1C) through a vertically adjacent eyelet, with the leading end of the suture exiting at point O-002 (FIG. 1D). The suture may be inserted at point I-003 (FIG. 1D) through a vertically adjacent eyelet, with the leading end of the suture exiting at point O-003 (FIG. 1C). The suture may then be inserted at point I-004 (FIG. 1C) through a vertically adjacent eyelet, with the leading end of the suture exiting at point O-004 (FIG. 1D). The suture may then be inserted through leaflet 108b at point I-005 (FIG. 1D) between two struts extending from the top of CAF 116, the leading end of the suture exiting at point O-005 (FIG. 1C). The suture may then be passed over one of the struts and inserted again through leaflet 108b at point I-006 (FIG. 1C), the leading end of the suture exiting at point O-006 (FIG. 1D).

At this stage, the trailing end of the suture is on the luminal (or inner) side of prosthetic heart valve 100, exiting through the lower left eyelet in the view of FIG. 1D. The trailing end of the suture may then be passed through the elongated eyelet at point I-007 (FIG. 1D), the trailing end exiting the elongated eyelet at point O-007 (FIG. 1C). The trailing end of the suture may be passed over a side of CAF 116 adjacent the elongated eyelet, and inserted through cuff 106 at point I-008 (FIG. 1C), exiting at point O-008 (FIG. 1D). The trailing end of the suture may again be passed over the side of CAF 116 adjacent the elongated eyelet and inserted again through the elongated eyelet at point I-009 (FIG. 1D), exiting the elongated eyelet at point O-009 (FIG. 1C). At this point, the trailing end of the suture may be left exiting at point O-009.

With the leading end of the suture still exiting at point O-006 (FIG. 1D), the leading end may be passed across the two struts at the top of CAF 116 and inserted through leaflet 108a at point I-010 (FIG. 1D), exiting at point O-010 (FIG. 1C). The leading end may then be passed over one of the struts connected to the top of CAF 116 and inserted through leaflet 108a at point I-011 (FIG. 1C), the leading end exiting at point O-011 (FIG. 1D). The leading end of the suture may then be inserted through an eyelet (top right eyelet in FIG. 1D) at point I-012, exiting the eyelet at point O-012 (FIG. 1C). The leading end of the suture may then be inserted through a vertically adjacent eyelet (bottom left eyelet in FIG. 1C) at point I-013, exiting the eyelet at point O-013 (FIG. 1D). The leading end of the suture may again be passed through a vertically adjacent eyelet (top right eyelet in FIG. 1D) at point I-014, exiting the eyelet at point O-014 (FIG. 1C). The leading end of the suture may again be passed through a vertically adjacent eyelet (bottom left eyelet in FIG. 1C) at point I-015, exiting the eyelet at point O-015 (FIG. 1D). The leading end of the suture may then be passed through the elongated eyelet at point I-016 (FIG. 1D), and may exit the elongated eyelet at point O-016 (FIG. 1C). The leading end of the suture may then be passed over a side of CAF 116 adjacent the elongated eyelet and inserted through cuff 106 at point I-017 (FIG. 1C), exiting at point O-017 (FIG. 1D). Finally, the leading end of the suture may again be passed over the side of CAF 116 adjacent the elongated eyelet and inserted through the elongated eyelet at point I-018 (FIG. 1D), the leading end exiting the elongated eyelet at point O-018 (FIG. 1C).

At this stage in the suturing process, the leading end of the suture exits the elongated eyelet at point O-018, while the trailing end still exits the elongated eyelet at point O-009. The two ends may be secured together, for example in a knot that is positioned within the elongated eyelet, to complete the suturing process. It will be appreciated that the suture pattern described in connection with FIGS. 1C-D may be obtained without following the exact suturing order described above. Further, although described with the use of a single suture, multiple sutures may be used to obtain the suture pattern described above.

Figure 2A:
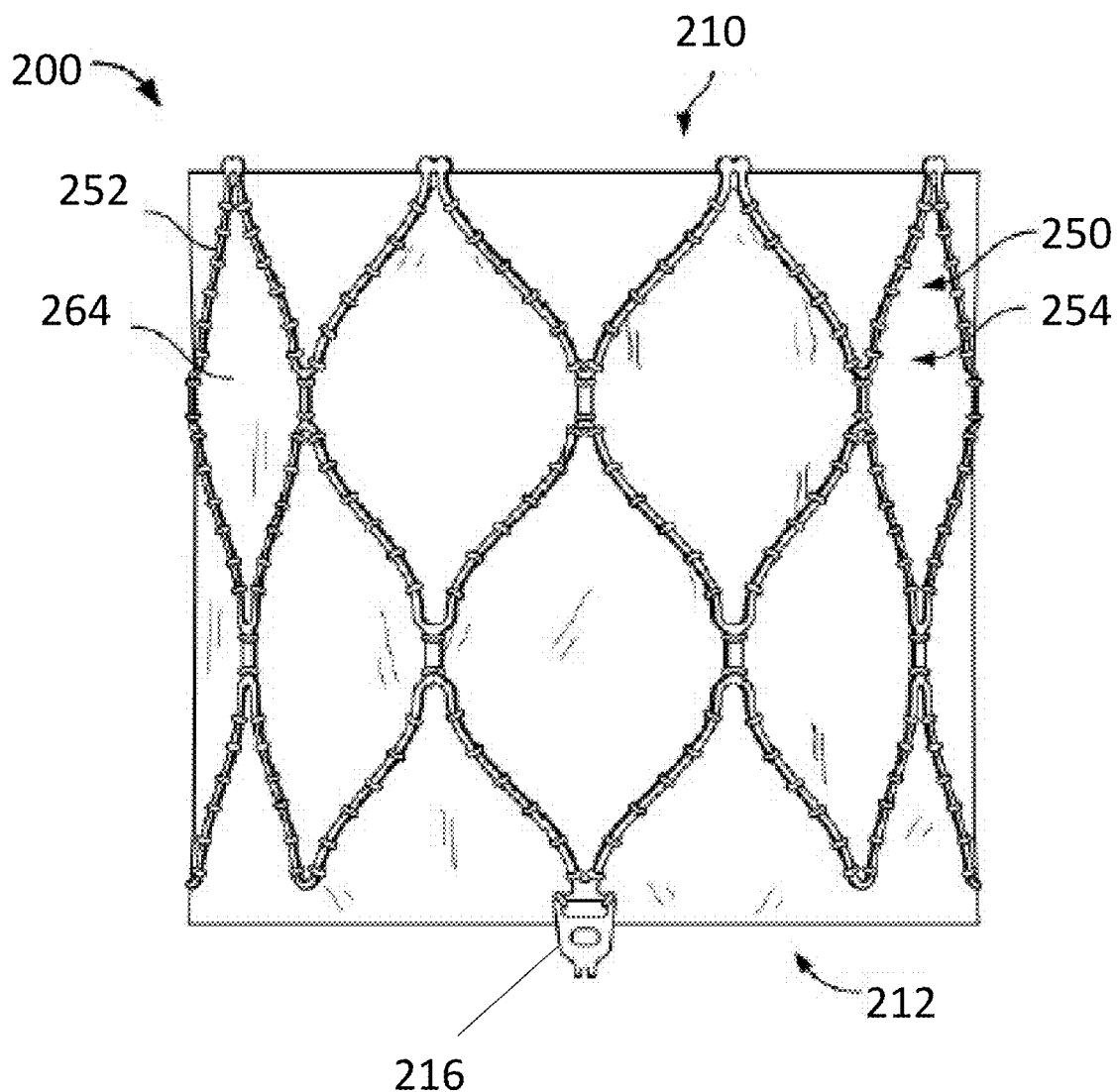
FIG. 2A is a side elevational view of another prosthetic heart valve according to the prior art.
Figure 2B:
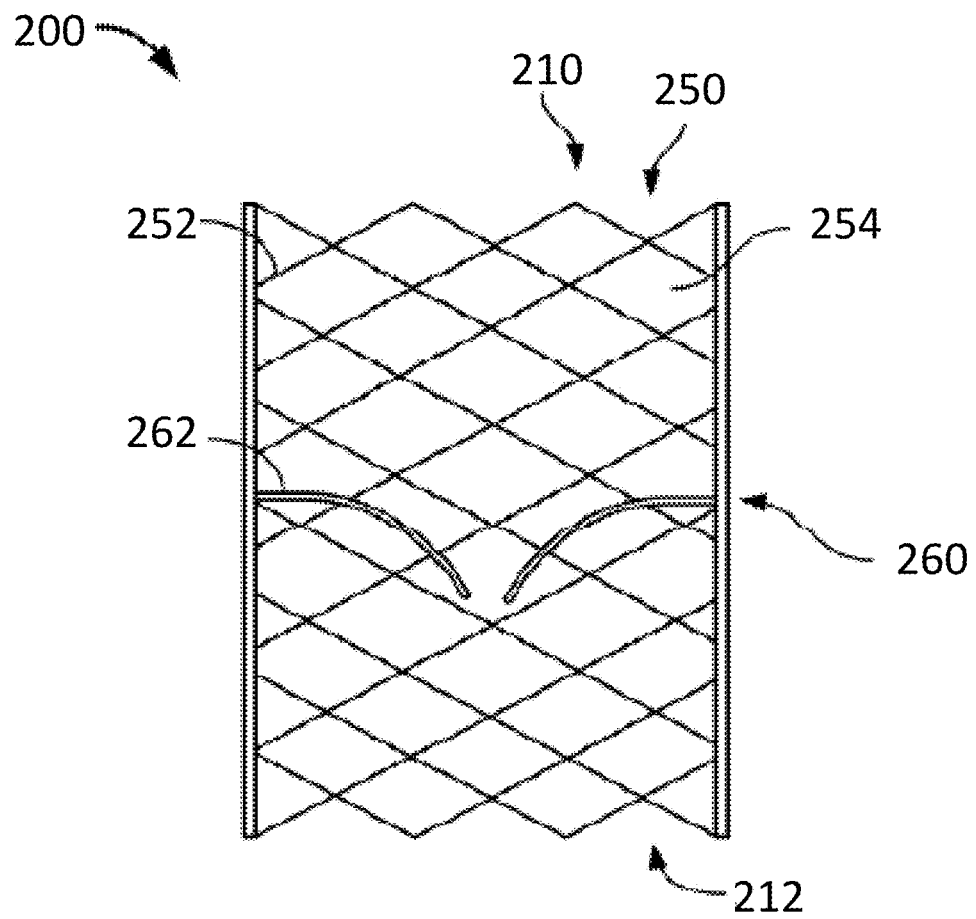
FIG. 2B is a highly schematic longitudinal cross-section of the prosthetic heart valve of FIG. 2A.

Although prosthetic heart valve 100 could be used to replace any of the native heart valves, it may be particularly suited for replacing the native aortic valve, as replacing other valves, such as the native mitral valve, may involve considerations that are additional to or different than those for aortic valve replacement. For example, FIGS. 2A and 2B are a side view and a longitudinal cross-sectional view, respectively, of a prosthetic heart valve 200 according to the prior art that may be particularly well-suited for replacing a native mitral valve. Generally, prosthetic valve 200 has a substantially cylindrical shape with inflow end 210 and outflow end 212. When used to replace the native mitral valve, prosthetic valve 200 may have a low profile so as to not obstruct the left ventricle outflow tract ("LVOT").

Prosthetic heart valve 200 may include stent 250, which may be formed from biocompatible materials that are capable of self-expansion, such as, for example, shape-memory alloys including nitinol. Stent 250 may include a plurality of struts 252 that form cells 254 connected to one another in one or more annular rows around the stent. Cells 254 may all be of substantially the same size around the perimeter and along the length of stent 250. Alternatively, cells 254 near inflow end 210 may be larger than the cells near outflow end 212. A plurality of CAFs 216 may be provided on the outflow end 212 of stent 250. Stent 250 may be expandable to provide a radial force to assist with positioning and stabilizing prosthetic heart valve 200 in the native valve annulus.

Prosthetic heart valve 200 may also include a substantially cylindrical valve assembly 260 including a plurality of leaflets 262 (FIG. 2B) attached to a cuff 264 and to CAFs 216 (FIG. 2A). Leaflets 262 replace the function of the native mitral valve leaflets. That is, leaflets 262 coapt with one another to function as a one way valve. The valve assembly 260 of prosthetic heart valve 200 may include two or three leaflets, but it is contemplated that prosthetic heart valve 200 may have more than three leaflets. Both cuff 264 and leaflets 262 may be wholly or partly formed of any suitable biological material, such as bovine or porcine pericardium, or polymers, such as PTFE, urethanes and the like. Valve assembly 260 may be secured to stent 250 by suturing to struts 252 or by using tissue glue, ultrasonic welding, or other suitable methods.

When prosthetic heart valve 200 is implanted in a patient, for example at the annulus of the native mitral valve, it is biased towards an expanded condition, providing radial force to anchor the valve in place. Generally, it is desirable for prosthetic mitral valves to avoid structure that extends too far into the left ventricle, as such structures may obstruct the LVOT. Also, it is generally preferable for a prosthetic mitral valve to avoid any structure that contacts the walls of the left ventricle, as such contact may cause conduction issues or disturbances in the heart.

Figure 3:
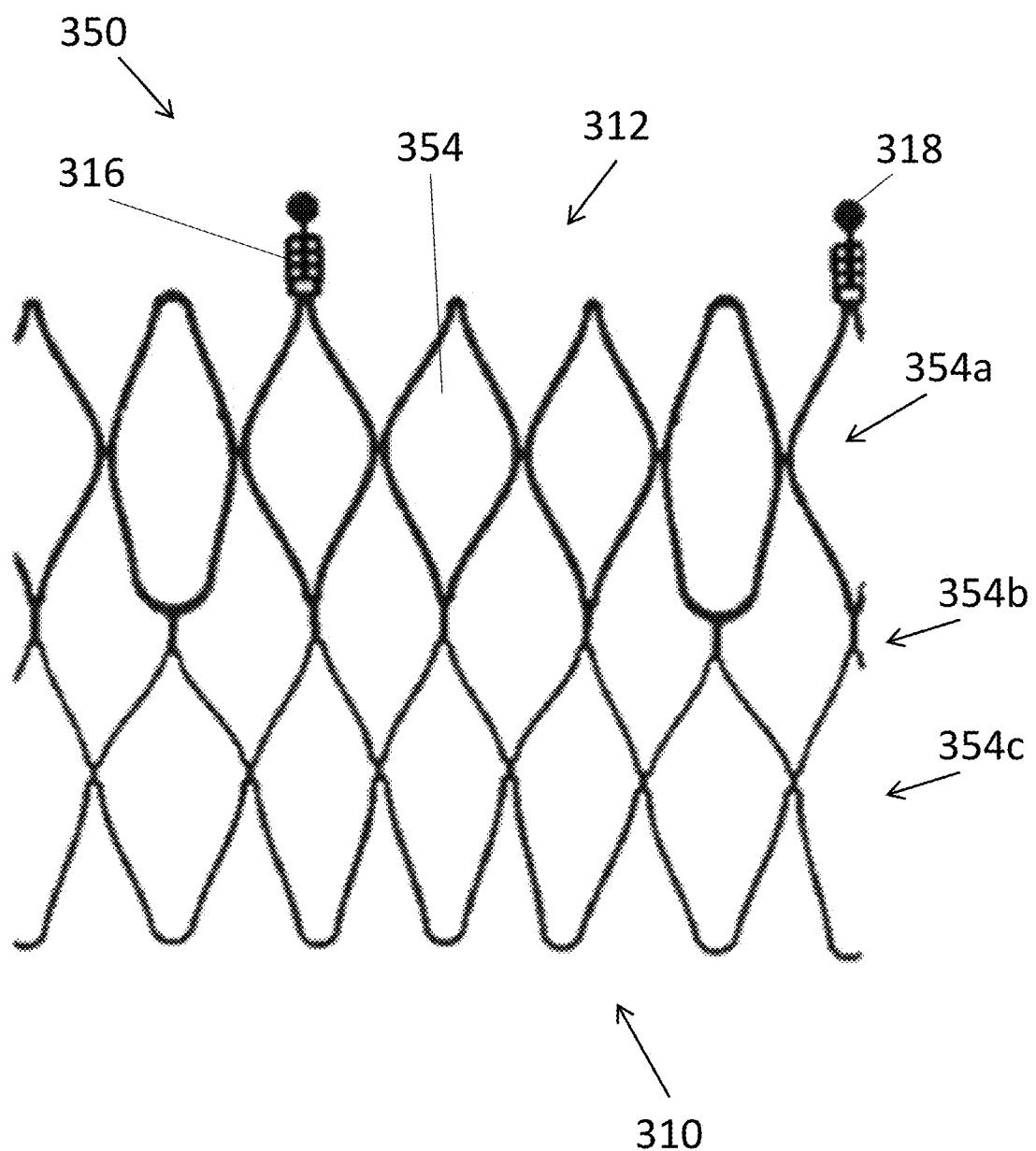
FIG. 3 is a schematic developed view of a portion of the stent of a prosthetic heart valve according to an embodiment of the disclosure.

FIG. 3 is a developed view of a stent 350 of a prosthetic mitral valve, illustrated as if cut longitudinally and laid out flat. Generally, stent 350 is similar to stent 250, and includes an inflow end 310 and an outflow end 312, although it should be understood that stent 350 is shown in an opposite orientation to how stent 250 is shown in FIG. 2A. While stent 250 includes two rows of cells 254, stent 350 includes three rows of cells 354, including a proximalmost row 354a nearest outflow end 312, a distalmost row 354c nearest inflow end 310, and an intermediate row 354b between the proximalmost and distalmost rows. A CAF 316 may extend in the outflow direction from selected cells in proximalmost row 354a, the CAFs providing a similar or identical function as other CAFs described above. Otherwise, stent 350 may be coupled to a cuff and leaflets similar to those described above in connection with prosthetic heart valves 100 and/or 200. If the prosthetic mitral valve incorporating stent 350 includes two leaflets, the stent will include two CAFs 316, although the number of leaflets need not exactly equal the number of the CAFs, so that, for example, two leaflets could be used with three CAFs. If the prosthetic mitral valve incorporating stent 350 includes three leaflets, the stent will include three CAFs 316. Each CAF 316 may also include a retaining element 318 that may serve a similar or identical function as retaining elements 118 of prosthetic heart valve 100.

Figure 4:
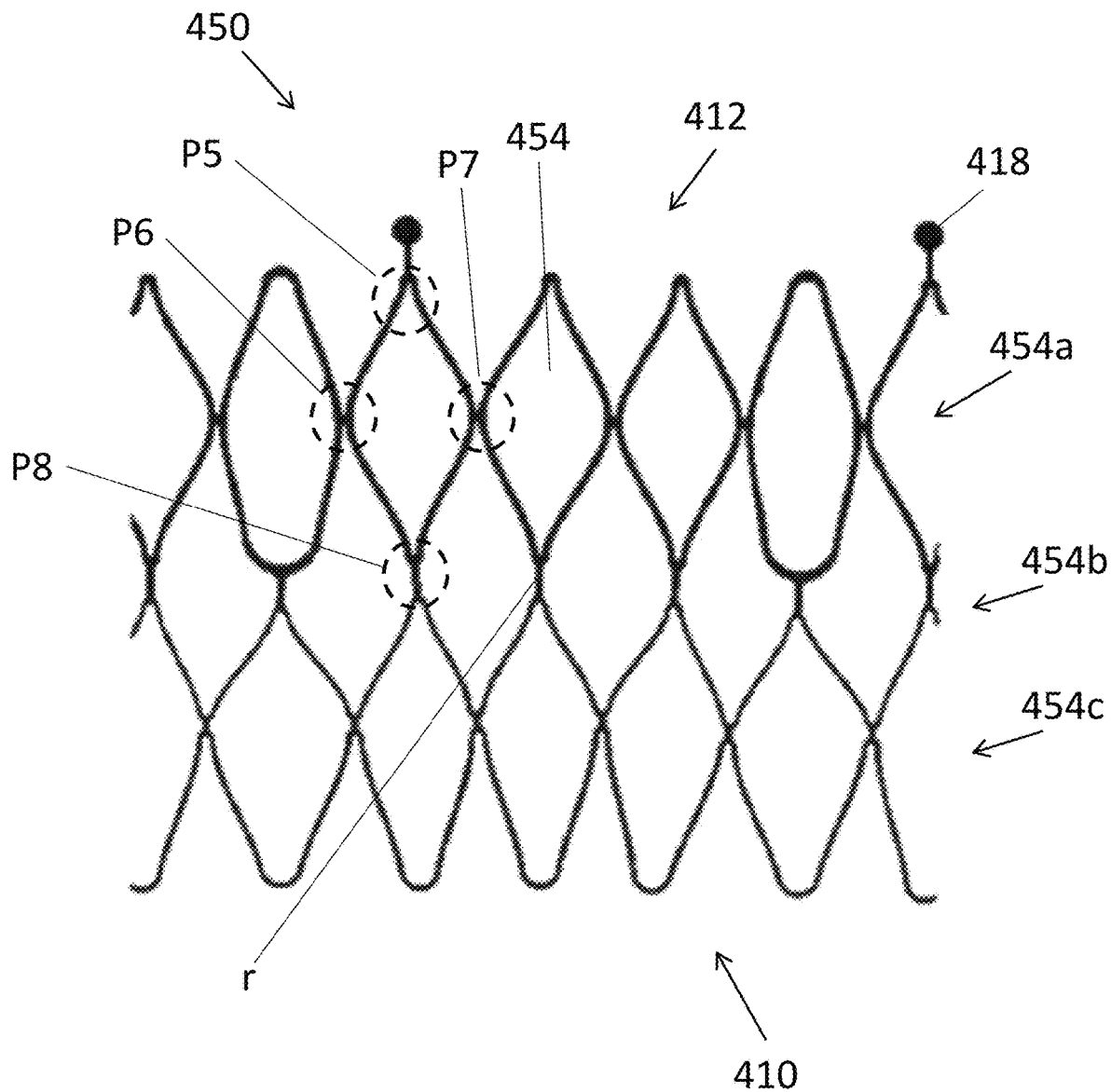
FIG. 4 is a schematic developed view of a portion of the stent of a prosthetic heart valve according to another embodiment of the disclosure.

It will be understood that when a prosthetic mitral valve incorporating stent 350 is properly implanted into a native mitral valve annulus, CAFs 316 and retaining elements 318 will extend toward and/or into the left ventricle of the patient. As noted above, it may be desirable to limit the structures extending into the left ventricle to help reduce LVOT obstruction and/or electrical conduction disturbances. Thus, FIG. 4 illustrates a stent 450 that is identical to stent 350, with the exception that the CAFs 316 have been removed. The length of the struts to which retainers 418 are attached may also be shorter than the combined length of the strut and CAF 316 of stent 350. In other words, the distance between the terminal end of retainer 418 and its corresponding cell apex may be less than the distance between the terminal end of retainer 318 and its corresponding cell apex. A prosthetic mitral valve that incorporates stent 450, compared to stent 350, may (i) provide additional flexibility regarding where leaflets can be attached to the stent, (ii) reduce the profile of the heart valve due to the elimination of the relatively bulky CAFs, and/or (iii) decrease the number of structures positioned outside the rows of cells and reduce interaction with anatomical structures in the left ventricle.

FIG. 4 is a developed view of stent 450, illustrated as if cut longitudinally and laid out flat. Stent 450 may be particularly useful in a prosthetic mitral valve. As with stent 350, stent 450 includes an inflow end 410, an outflow end 412, and three rows 454a-454c of cells 454. However, as noted above, stent 450 does not include CAFs that have similar structure to CAFs 316, although stent 450 may still include retaining elements 418 similar to retaining elements 318. A prosthetic heart valve incorporating stent 450 may include a cuff similar to cuff 264, and a valve assembly with leaflets similar to valve assembly 260 and leaflets 262. However, because stent 450 eliminates structures similar to the CAFs 316 of stent 350, the attachment of the leaflets to the stent may be different than in stents 102, 250, and 350. FIG. 4 illustrates various potential locations for coupling portions of two adjacent leaflets directly to struts of stent 450 via suturing. However, as will become clear, other locations in which struts intersect similarly to the identified locations in FIG. 4 may be suitable for coupling leaflets to the stent 450, using the same or different suture patterns as described below for the identified locations. A first connection location P5 is shown at a "Y"-shaped intersection of three struts, the "Y"-shaped intersection being formed by two struts of a cell 454 in row 454a from which retaining element 418 extends, with the third strut of the "Y"-shape being a part of the retaining element. A second connection location P6 is shown at an "X"-shaped intersection of four struts, the "X"-shaped intersection being formed by two struts of a first cell 454 in first row 454a, and two struts of an adjacent second cell in the first row. A third connection location P7 is substantially similar to connection location P6, with the main difference being that connection location P6 is positioned in a first circumferential direction from a retaining element 418, while connection location P7 is positioned in a second circumferential direction opposite the first circumferential direction from the retaining element. In other words, connection location P7 is also at an "X"-shaped intersection of four struts, the "X"-shaped intersection being formed by two struts of a first cell 454 in first row 454a, and two struts of an adjacent second cell in the first row. A fourth attachment location P8 is shown at a generally "X"-shaped intersection of four struts, the "X"-shaped intersection being formed by two struts of a first cell 454 in intermediate row 454b, and two struts of an adjacent second cell in the intermediate row. Although attachment location P8 may be referred to as "X"-shaped, in the illustrated example, attachment location P8 includes a strut connector or runner r that extends in the longitudinal direction between the cells 454 in rows 454a and 454c. Otherwise, attachment location P8 may be circumferentially aligned with attachment location P5, but positioned circumferentially between attachment locations P6 and P7, and closer to the inflow end 410 of stent 450 than each of attachment locations P5, P6, and P7. Only one of these connection locations is used to couple the ends of any pair of adjacent leaflets to stent 450. Further, since stent 450 has a repeating circumferential structure, the ends of other pairs of adjacent leaflets can be coupled together and to the stent in a similar fashion. For example, if two leaflets are coupled to stent 450, and one end of the leaflet pair is coupled to the stent at attachment location P5, the other end of the leaflet pair is preferably coupled to a corresponding location at the diametrically opposed location on the stent. The same is preferably true for the other attachment locations P6, P7, and P8. In the illustrated example, attachment locations P5, P6, P7, and P8 each include at least one strut that is part of a cell 454 in the first circumferential row 454a. However, it should be understood that in some embodiments, the same valve could be attached to stent 450 using different attachment sites for each attachment and/or different suture patterns for each attachment. For example, in some situations it may be preferable to attach a leaflet pair to two of the P8 locations on opposite sides of stent 450, but using different suture patterns, while in still other situations it may be preferable to attach one end of a leaflet pair to a P8 location and the other end of the leaflet pair to a P7 location on a different portion of the stent, using either the same or different suture patterns.

Figure 5A:
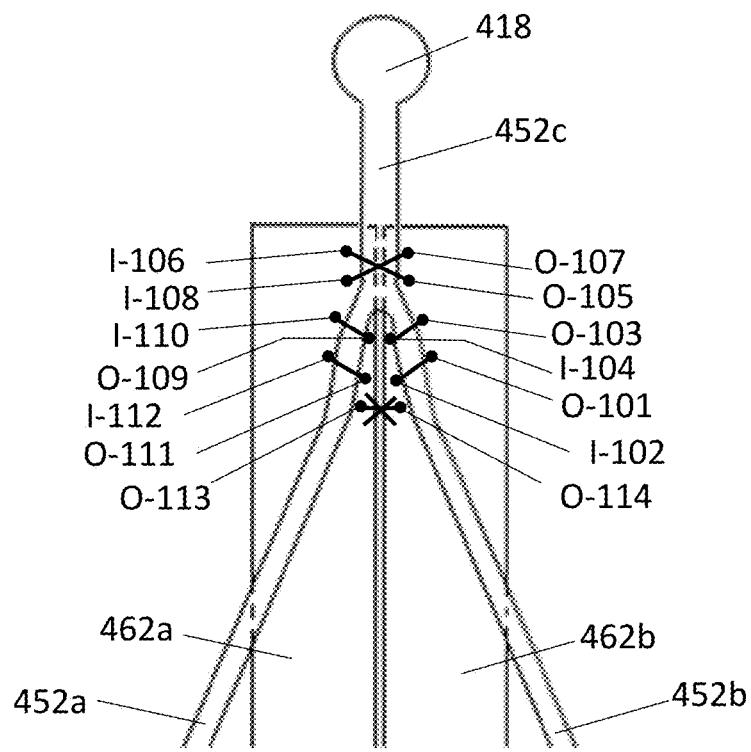
FIG. 5A is a schematic view of a suture pattern on the stent of FIG. 4, shown from the exterior of the stent.
Figure 5B:
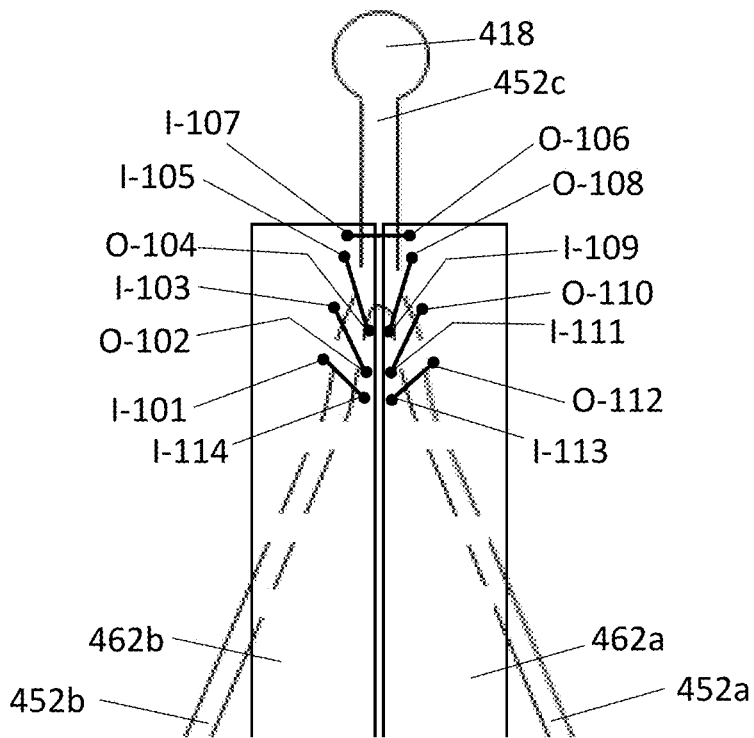
FIG. 5B is a schematic view of the suture pattern of FIG. 5A, shown from the interior of the stent of FIG. 4.

FIGS. 5A-B illustrate a suture pattern for suturing portions of two adjacent leaflets 462a, 462b to connection location P5 shown in FIG. 4. As noted above, the connection location P5 is at a "Y"-shaped intersection of two struts 452a, 452b of a cell 454 in row 454a from which retaining element 418 extends, with the third strut 452c of the "Y"-shape connecting an apex of the cell to the retaining element. FIG. 5A illustrates the suture pattern as viewed from the exterior of stent 450, and FIG. 5B illustrates the suture pattern as viewed from the interior of the stent. It should be understood that, although a cuff is not illustrated, typically a cuff would be positioned between the leaflets 462a, 462b and stent 450.

The suture pattern of FIGS. 5A-B is described and illustrated with reference to part numbers having the format of I-101 or O-101. The "I" refers to an end of a suture being passed inwardly through the cuff and/or leaflets 462a, 462b in the particular view being shown, the "O" refers to an end of the suture being passed outwardly through the cuff and/or leaflets in the particular view being shown, and the number (e.g., 101) refers to the sequence of the particular stitch being described starting with "101." Referring to FIGS. 5A-B, the suture pattern may begin by passing the leading end of the suture through leaflet 462b at point I-101 (FIG. 5B), with the leading end of the suture exiting at point O-101 (FIG. 5A). The leading end of the suture may be passed over strut 452b and inserted through leaflet 462b at point I-102 (FIG. 5A), the leading end exiting leaflet 462b at point O-102 (FIG. 5B). The leading end of the suture may then be inserted through leaflet 462b at point I-103 (FIG. 5B) on the opposite side of strut 452b, the leading end exiting leaflet 462b at point O-103 (FIG. 5A). The leading end of the suture may again be passed over strut 452b and inserted through leaflet 462b at point I-104 (FIG. 5A), exiting leaflet 462b at point O-104 (FIG. 5B). The leading end of the suture may then be inserted through leaflet 462b at point I-105 (FIG. 5B) on the opposite side of strut 452b, exiting leaflet 462b at point O-105 (FIG. 5A). The leading end of the suture may then be passed over strut 452c and inserted through leaflet 462a at point I-106 (FIG. 5A), the leading end exiting leaflet 462a at point O-106 (FIG. 5B). The leading end of the suture may then be inserted through leaflet 462b at point I-107 (FIG. 5B) on the opposite side of strut 452c, exiting leaflet 462b at point O-107 (FIG. 5B). The leading end of the suture may again be passed over strut 452c and inserted through leaflet 462a at point I-108 (FIG. 5A), the leading end exiting leaflet 462a at point O-108 (FIG. 5B). The leading end of the suture may then be inserted through leaflet 462a at point I-109 (FIG. 5B) on the opposite side of strut 452a, exiting leaflet 462a at point O-109 (FIG. 5A). The leading end of the suture may then be passed over strut 452a and inserted through leaflet 462a at point I-110 (FIG. 5A), exiting leaflet 462a at point O-110 (FIG. 5B). The leading end of the suture may again be inserted through leaflet 462a at point I-111 (FIG. 5B) on the opposite side of strut 452a, exiting leaflet 462a at point O-111 (FIG. 5A). The leading end of the suture may then be passed over strut 452a and inserted through leaflet 462a at point I-112 (FIG. 5A), the leading end exiting leaflet 462a at point O-112 (FIG. 5B). The leading end of the suture may then be inserted through leaflet 462a at point I-113 (FIG. 5B) again on the opposite side of strut 452a, the leading end exiting leaflet 462a at point O-113 (FIG. 5A).

At this stage, the trailing end of the suture is still on the luminal side of the leaflets, exiting leaflet 462b at point I-101 (FIG. 5B). The trailing end of the suture may be inserted through leaflet 462b at point I-114 (FIG. 5B) on the opposite side of strut 452b, the trailing end of the suture exiting leaflet 462b at point O-114 (FIG. 5A). With the trailing end of the suture exiting leaflet 462b at point O-114 (FIG. 5A) and the leading end of the suture exiting leaflet 462a at point O-113 (FIG. 5A), the leading and trailing ends may be secured together, for example, in a knot that is positioned between struts 452a and 452b, to complete the suturing process. It will be appreciated that the suture pattern described in connection with FIGS. 5A-B may be obtained without following the exact suturing order described above. Further, although described with the use of a single suture, multiple sutures may be used to obtain the suture pattern described above.

Figure 6A:
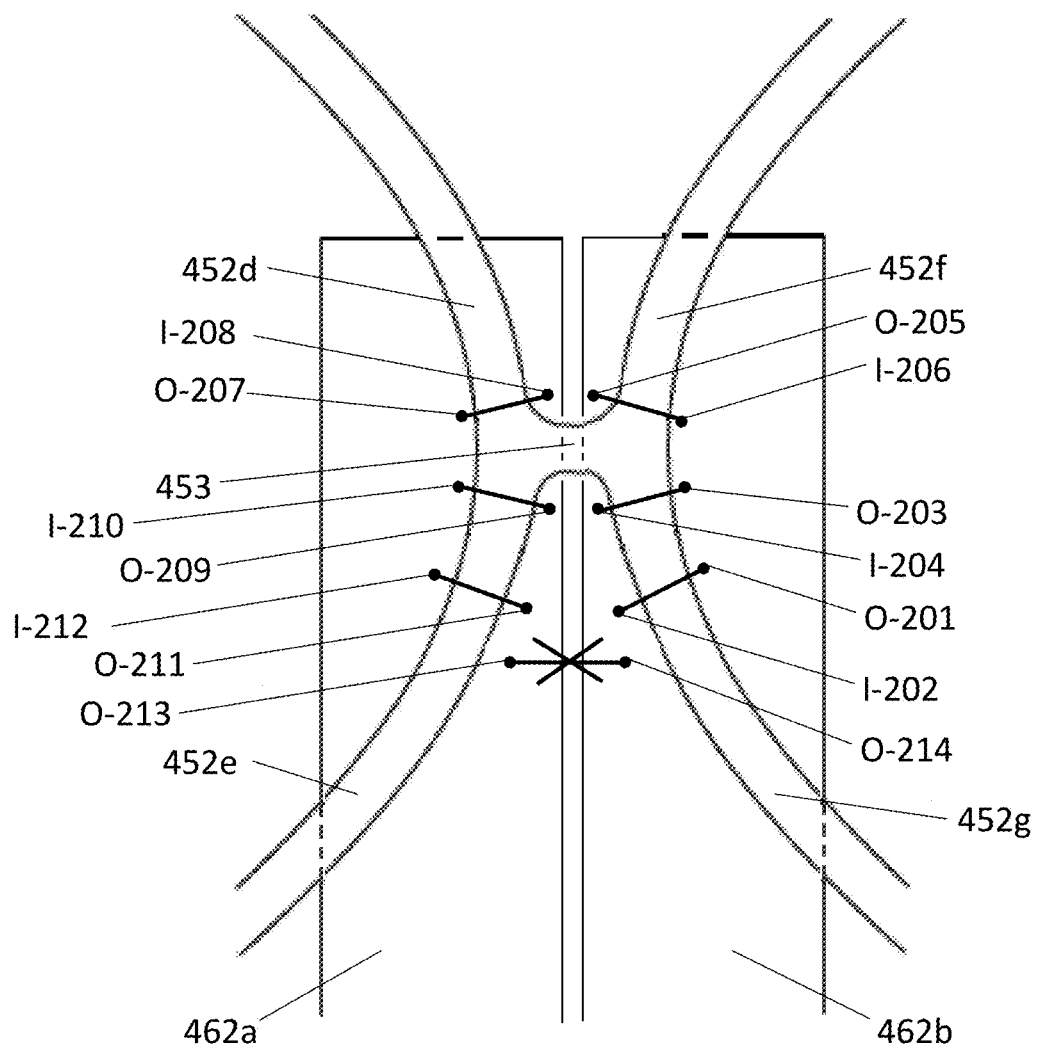
FIG. 6A is a schematic view of another suture pattern on the stent of FIG. 4, shown from the exterior of the stent.
Figure 6B:
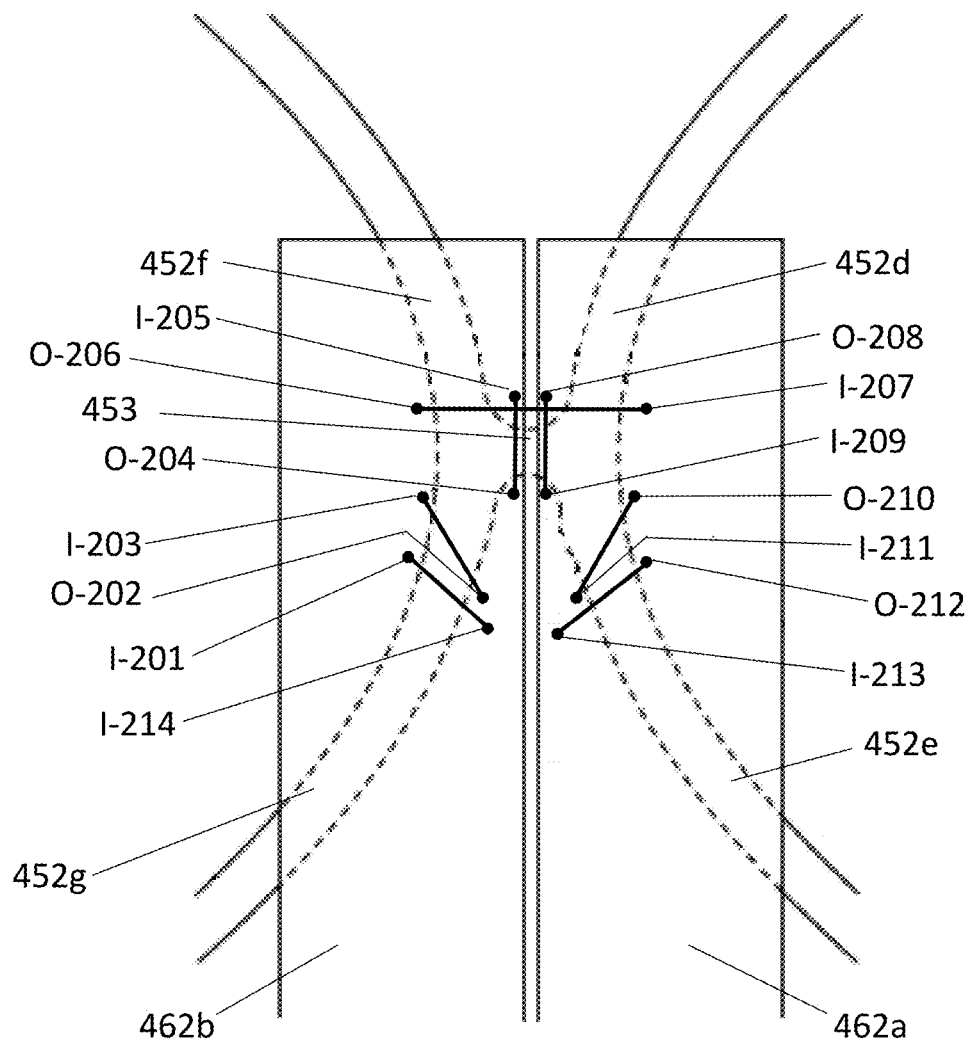
FIG. 6B is a schematic view of the suture pattern of FIG. 6A, shown from the interior of the stent of FIG. 4.

FIGS. 6A-B illustrate a suture pattern for suturing portions of two adjacent leaflets 462a, 462b to connection location P6 shown in FIG. 4. As noted above, the connection location P6 is at a "X"-shaped intersection of two struts 452d, 452e of a first cell 454 in row 454a with two struts 452f, 452g of a second cell in row 454a adjacent the first cell. FIG. 6A illustrates the suture pattern as viewed from the exterior of stent 450, and FIG. 6B illustrates the suture pattern as viewed from the interior of the stent. It should be understood that, although a cuff is not illustrated, typically a cuff would be positioned between the leaflets 462a, 462b and stent 450. Although the suture pattern shown in FIGS. 6A-B is explained with reference to the "X"-shaped intersection at connection location P6, the same suture pattern may be used for the "X"-shaped intersections at connection locations P7 and P8, as those connection locations have a similar strut structure.

The suture pattern of FIGS. 6A-B is described and illustrated with reference to part numbers having the format of I-201 or O-201. The "I" refers to an end of a suture being passed inward through the cuff and/or leaflets 462a, 462b in the particular view being shown, the "O" refers to an end of the suture being passed outwardly through the cuff and/or leaflets in the particular view being shown, and the number (e.g., 201) refers to the sequence of the particular stitch being described starting with "201." Referring to FIGS. 6A-B, the suture pattern may begin by passing the leading end of the suture through leaflet 462b at point I-201 (FIG. 6B), with the leading end of the suture exiting at point O-201 (FIG. 6A). The leading end of the suture may be passed over strut 452g and inserted through leaflet 462b at point I-202 (FIG. 6A), the leading end exiting leaflet 462b at point O-202 (FIG. 6B). The leading end of the suture may then be inserted through leaflet 462b at point I-203 (FIG. 6B) on the opposite side of strut 452g, exiting leaflet 462b at point O-203 (FIG. 6A). The leading end of the suture may again be passed over strut 452g and inserted through leaflet 462b at point I-204 (FIG. 6A), the leading end exiting leaflet 462b at point O-204 (FIG. 6B). The leading end of the suture may then be inserted through leaflet 462b at point I-205 (FIG. 6B) on the other side of strut connector 453 where struts 452d-g intersect, the leading end of the suture exiting leaflet 462b at point O-205 (FIG. 6A). The leading end of the suture may then be passed over strut 452f and inserted through leaflet 462b at point I-206 (FIG. 6A), the leading end exiting leaflet 462b at point O-206 (FIG. 6B). The leading end of the suture may then be inserted through leaflet 462a at point I-207 (FIG. 6B) across struts 452d and 452f, exiting leaflet 462a at point O-207 (FIG. 6A). The leading end of the suture may be passed over strut 452d and through leaflet 462a at point I-208 (FIG. 6A), exiting leaflet 462a at point O-208 (FIG. 6B). The leading end of the suture may then be inserted through leaflet 462a at point I-209 (FIG. 6B) on the other side of strut connector 453, exiting leaflet 462a at point O-209 (FIG. 6A). The leading end of the suture may then be passed over strut 452e and through leaflet 462a at point I-210 (FIG. 6A), the leading end exiting leaflet 462a at point O-210 (FIG. 6B). The leading end of the suture may then be inserted through leaflet 462a at point I-211 (FIG. 6B) on the other side of strut 452e, exiting leaflet 462a at point O-211 (FIG. 6A). The leading end of the suture may then be passed over strut 452e and through leaflet 462a at point I-212 (FIG. 6A), the leading end exiting leaflet 462a at point O-212 (FIG. 6B). The leading end of the suture may then be inserted through leaflet 462a at point I-213 (FIG. 6B) on the other side of strut 452e, exiting leaflet 462a at point O-213 (FIG. 6A).

At this stage, the trailing end of the suture is still on the luminal side of the leaflets, exiting leaflet 462b at point I-201 (FIG. 6B). The trailing end of the suture may be inserted through leaflet 462b at point I-214 (FIG. 6B) on the opposite side of strut 452*g*, exiting leaflet 462*b* at point O-214 (FIG. 6A). With the trailing end of the suture exiting leaflet 462*b* at point O-214 (FIG. 6A) and the leading end of the suture exiting leaflet 462*a* at point O-213 (FIG. 6A), the leading and trailing ends may be secured together, for example, in a knot that is positioned between struts 452*e* and 452*g*, to complete the suturing process. It will be appreciated that the suture pattern described in connection with FIGS. 6A-B may be obtained without following the exact suturing order described above. Further, although described with the use of a single suture, multiple sutures may be used to obtain the suture pattern described above.

As noted above, the suture pattern for attaching two adjacent leaflets 462*a*, 462*b* to stent 450 at location P6, as described above, may be substantially the same as or identical to the suture pattern for attaching two adjacent leaflets to locations P7 or P8. However, although locations P6 and P7 are structurally identical (or nearly identical), location P8 may have slight structural differences compared to locations P6 and P7. For example, location P8, while still being formed at the intersection of two struts of a cell 454 in row 454*b* with two struts of an adjacent cell 454 in row 454*b*, may include a runner r that is longer in the longitudinal direction of stent 454 compared to strut connector 453 in locations P6 and P7. It should be understood that, in this context, the longitudinal direction refers to the direction extending from inflow end 410 to outflow end 412 of stent 450, or vice versa. It should be understood that, depending on the shape of stent 450 when it is in the expanded condition or otherwise in an implanted condition, the choice of particular connection locations may be driven, at least in part, by the shape of the stent at those locations and the corresponding geometry of the leaflets.

As noted above, stent 450 and the suture patterns described above enable not only the elimination of CAFs similar to CAFs 316 of stent 350, but also provide for flexibility in attachment locations of leaflets 462*a*, 462*b* to the stent. For example, attachment location P5 allows leaflets 462*a*, 462*b* to be positioned nearer outflow end 412 compared to attachment locations P6, P7, and P8, while attachment locations P6 and P7 provide intermediate attachment locations in the longitudinal direction compared to locations P5 and P8. In addition, attachment locations P6 and P7 enable attachment of leaflets 462*a*, 462*b* in either circumferential direction of stent 450 compared to attachment locations P5 and P8. The foregoing attachment options allow the prosthetic leaflets to be shifted in different directions relative to the native prosthetic valve annulus, which may assist in reducing LVOT obstruction, increasing sealing between the prosthetic heart valve and the native valve annulus, and/or optimizing prosthetic leaflet function. In addition, the various possible attachment locations enable other features to be incorporated into stent 450, while providing a leaflet attachment location that minimizes interference with such additional structures. For example, additional stent features such as clips, anchor arms, or the like that assist in capturing the native valve leaflets may be added to stent 450 at positions near where CAFs 316 of stent 350 are positioned. In that case, it may be preferable to attach the prosthetic leaflets to locations P6, P7, or P8, since location P5 would be near to, and could otherwise undesirably interfere with, the added anchor arms. In other examples, it may be desirable to provide stent 450 with a flange, such as a braided flange, that is to be positioned in the left atrium to help prevent migration of the prosthetic mitral valve into the left ventricle during operation. With such a braided flange, it may be desirable to provide braid connectors on stent 450 to attach the braided flange to the stent. Such braid connectors desirably may be positioned near the axial center of stent 450 in some embodiments. In those embodiments, it may be desirable to attach prosthetic leaflets 462*a*, 462*b* to attachment locations P5, P6, or P7, which are relatively far from the axial center of the stent compared to location P8. However, the broader implication is that the particular attachment sites of the leaflets can be picked based on various considerations which may be different based on the features of the prosthetic heart valve, allowing for significant flexibility in design choice.

According to an aspect of the disclosure, a prosthetic mitral valve comprises:

a collapsible stent including a plurality of struts, a plurality of cells arranged in circumferential rows, the circumferential rows including a first row at an outflow end of the stent and a second row at an inflow end of the stent, and a plurality of strut intersections where at least two of the struts connect to one another;

a cuff attached to the stent; and a prosthetic valve assembly adapted to allow blood to flow from the inflow end of the stent toward the outflow end of the stent and to restrict blood from flowing from the outflow end of the stent toward the inflow of the stent, the prosthetic valve assembly including a first prosthetic leaflet having a first end attached directly to a first one of the strut intersections, and a second prosthetic leaflet having a first end attached directly to the first strut intersection, wherein the first strut intersection is partially formed of one of the struts of one of the cells in the first row; and/or a single suture attaching both the first end of the first prosthetic leaflet and the first end of the second prosthetic leaflet to the first strut intersection; and/or the stent includes at least one retaining element sized and shaped to cooperate with a corresponding retaining structure of a delivery device, the retaining element including a strut extending from an apex of one of the cells in the first row of cells; and/or the first strut intersection is a "Y"-shaped intersection formed by the strut of the retaining element, and two struts that form the apex of the one cell in the first row of cells; and/or a single suture attaching both the first end of the first prosthetic leaflet and the first end of the second prosthetic leaflet to the "Y"-shaped intersection, the single suture having a leading end and a trailing end; and/or the leading end of the suture is secured to the trailing end of the suture in a knot; and/or the knot is positioned between the two struts that form the apex of the one cell in the first row of cells; and/or the first strut intersection is an "X"-shaped intersection formed by four struts; and/or the four struts forming the "X"-shaped intersection include first and second struts of a first cell in the first row, and third and fourth struts of a second cell in the first row circumferentially adjacent the first cell, the first and second struts being joined to the third and fourth struts via a strut connector; and/or a single suture attaching both the first end of the first prosthetic leaflet and the first end of the second prosthetic leaflet to the "X"-shaped intersection, the single suture having a leading end and a trailing end; and/or the leading end of the suture is secured to the trailing end of the suture in a knot; and/or the knot is positioned between the first cell and the second cell; and/or the stent includes an intermediate circumferential row of cells positioned between the first row and the second row; and/or the first strut intersection is an "X"-shaped intersection formed by four struts, the four struts including first and second struts of a first cell in the intermediate row, and third and fourth struts of a second cell in the intermediate row circumferentially adjacent the first cell, the first and second struts being joined to the third and fourth struts via a strut connector; and/or the first strut also forms a portion of a third cell in the first row, and the third strut also forms a portion of a fourth cell in the first row; and/or a single suture attaching both the first end of the first prosthetic leaflet and the first end of the second prosthetic leaflet to the "X"-shaped intersection, the single suture having a leading end and a trailing end; and/or the leading end of the suture is secured to the trailing end of the suture in a knot; and/or the knot is positioned between the second strut and the fourth strut; and/or the first prosthetic leaflet has a second end attached directly to a second one of the strut intersections, and the second prosthetic leaflet has a second end attached directly to the second strut intersection; and/or the first strut intersection has a first position on the stent and the second strut intersection has a second position on the stent, the first position being diametrically opposed to the second position.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic mitral valve, comprising:
a collapsible stent including a plurality of struts, a plurality of cells arranged in circumferential rows, the circumferential rows including a first row at an outflow end of the stent and a second row at an inflow end of the stent, and a plurality of strut intersections where at least two of the struts connect to one another;
a cuff attached to the stent;
a prosthetic valve assembly adapted to allow blood to flow from the inflow end of the stent toward the outflow end of the stent and to restrict blood from flowing from the outflow end of the stent toward the inflow of the stent, the prosthetic valve assembly including a first prosthetic leaflet having a first end attached directly to a first one of the strut intersections, and a second prosthetic leaflet having a first end attached directly to the first strut intersection; and
a single suture attaching both the first end of the first prosthetic leaflet and the first end of the second prosthetic leaflet to the first strut intersection,
wherein the first strut intersection is partially formed of one of the struts of one of the cells in the first row,
wherein the stent includes at least one retaining element sized and shaped to cooperate with a corresponding retaining structure of a delivery device, the retaining element including a strut extending from an apex of one of the cells in the first row of cells,
wherein the first strut intersection is a "Y"-shaped intersection consists of the strut of the retaining element, and two struts that form the apex of the one cell in the first row of cells,
wherein, on a luminal side of the stent, a first segment of the single suture extends from the first end of the first prosthetic leaflet to the first end of the second prosthetic leaflet behind the strut of the retaining element, a second segment of the single suture extends on the first end of the first prosthetic leaflet behind one of the two struts forming the apex, and a third segment of the single suture extends on the first end of the second prosthetic leaflet behind other of the two struts forming the apex.

2. The prosthetic mitral valve of claim 1, wherein the leading end of the suture is secured to the trailing end of the suture in a knot.

3. The prosthetic mitral valve of claim 2, wherein the knot is positioned between the two struts that form the apex of the one cell in the first row of cells.

4. The prosthetic mitral valve of claim 1, wherein the stent includes an intermediate circumferential row of cells positioned between the first row and the second row.

5. The prosthetic mitral valve of claim 1, wherein, on an abluminal side of the stent, fourth and fifth segments of the single suture extend in an X-formation across the strut of the retaining element, a sixth segment of the single suture attaches the first end of the first prosthetic leaflet to the one of the two struts forming the apex, and a seventh segment of the single suture attaches the first end of the second prosthetic leaflet to the other of the two struts forming the apex.

* * * * *